(12) United States Patent
Hiramoto et al.

(10) Patent No.: US 9,375,501 B2
(45) Date of Patent: Jun. 28, 2016

(54) DEODORANT COMPOSITION

(75) Inventors: Tadahiro Hiramoto, Hiratsuka (JP);
Kenichiro Shiroyama, Hiratsuka (JP);
Hiroyasu Kumamoto, Hiratsuka (JP)

(73) Assignee: TAKASAGO INTERNATIONAL CORPORATION, Tokyo (JP)

(*) Notice: Subject to any disclaimer, the term of this patent is extended or adjusted under 35 U.S.C. 154(b) by 0 days.

(21) Appl. No.: 12/293,661

(22) PCT Filed: Mar. 22, 2007

(86) PCT No.: PCT/JP2007/056753
§ 371 (c)(1),
(2), (4) Date: Sep. 19, 2008

(87) PCT Pub. No.: WO2007/111362
PCT Pub. Date: Oct. 4, 2007

(65) Prior Publication Data
US 2010/0158840 A1 Jun. 24, 2010

(30) Foreign Application Priority Data
Mar. 22, 2006 (JP) ................. 2006-079559

(51) Int. Cl.
*A61K 8/66* (2006.01)
*A61L 9/01* (2006.01)
*A61K 8/19* (2006.01)
*A61K 8/20* (2006.01)
*A61K 8/36* (2006.01)
*A61K 8/365* (2006.01)
*A61K 8/368* (2006.01)
*A61K 8/37* (2006.01)
*A61K 8/49* (2006.01)
*A61K 8/60* (2006.01)
*A61K 8/97* (2006.01)
*A61L 9/013* (2006.01)
*A61Q 15/00* (2006.01)

(52) U.S. Cl.
CPC ... *A61L 9/01* (2013.01); *A61K 8/19* (2013.01);
*A61K 8/20* (2013.01); *A61K 8/36* (2013.01);
*A61K 8/365* (2013.01); *A61K 8/368* (2013.01);
*A61K 8/375* (2013.01); *A61K 8/498* (2013.01);
*A61K 8/602* (2013.01); *A61K 8/97* (2013.01);
*A61L 9/013* (2013.01); *A61Q 15/00* (2013.01)

(58) Field of Classification Search
CPC ............ A61K 8/19; A61K 8/347; A61L 9/00;
A61L 9/01; A61L 9/013; A61Q 15/00
See application file for complete search history.

(56) References Cited

U.S. PATENT DOCUMENTS

| | | | |
|---|---|---|---|
| 5,804,170 A * | 9/1998 | Negishi et al. | 424/65 |
| 5,833,864 A * | 11/1998 | Miller et al. | 210/724 |
| 6,080,391 A * | 6/2000 | Tsuchiya et al. | 424/65 |
| 6,174,521 B1 * | 1/2001 | Li et al. | 424/65 |
| 6,294,161 B1 * | 9/2001 | Hiramoto et al. | 424/76.1 |
| 6,551,625 B1 | 4/2003 | Hilaire et al. | |
| 6,605,288 B1 * | 8/2003 | Okawa et al. | 424/401 |
| 2007/0003492 A1 * | 1/2007 | Kitahata et al. | 424/49 |

FOREIGN PATENT DOCUMENTS

| | | |
|---|---|---|
| CN | 1732019 A | 2/2006 |
| DE | 198 31 798 A1 | 1/2000 |
| EP | 1 064 956 A2 | 1/2001 |
| EP | 1 426 380 A1 | 6/2004 |
| EP | 1 520 576 A2 | 4/2005 |
| EP | 1 561 476 * | 8/2005 |
| EP | 1 561 476 A1 | 8/2005 |
| EP | 1561476 A1 * | 8/2005 |
| JP | 64-016713 A | 1/1989 |
| JP | 4-219136 A | 8/1992 |
| JP | 4-346831 A | 12/1992 |
| JP | 5-092135 A | 4/1993 |
| JP | 5-269164 A | 10/1993 |
| JP | 9-038183 A | 2/1997 |
| JP | 11-319051 A | 11/1999 |
| JP | 2002-004172 A | 1/2002 |
| JP | 2003-95905 A | 4/2003 |
| JP | 2004-167218 A | 6/2004 |
| JP | 2004-242516 A | 9/2004 |
| JP | 2005143770 A | 6/2005 |
| WO | WO 2004039345 A1 * | 5/2004 |
| WO | WO 2005026048 A1 * | 3/2005 |

OTHER PUBLICATIONS

Derwent Abstract: Kosuge et al. JP 02298345, issued Dec. 10, 1990.*
Derwent abstract for JP 2004204085.*
Gauillard et al.; "Oxidation of Chlorogenic Acid, Catechins, and 4-Methylcatechol in Model Solutions by Combination of Pear (*Pyrus communis* Cv. Williams) Polyphenol Oxidase and Peroxidase: A possible Involvement of Peroxidase in Enzymatic Browning," 1997, ACS, Journal of Agriculture and Food Chemistry, vol. 45, No. 7, pp. 2472-2476.*
Harborne, Jeffery; "Phytochemical Dictionary: A Handbook of Bioactive Compounds from Plants," 1999, Taylor & Francis; part IV Phenolics General Introduction, pp. 1-5 as provided.*

(Continued)

*Primary Examiner* — Suzanne Ziska
*Assistant Examiner* — Ivan Greene
(74) *Attorney, Agent, or Firm* — Sughrue Mion, PLLC

(57) ABSTRACT

The present invention relates to a deodorant composition containing (a) a polyphenol compound or a plant extract containing a polyphenol compound, (b) a basic substance, and (c) a metal salt. The deodorant composition of the present invention is capable of providing a deodorizing effect in a short period of time when it is applied to a malodor source, is capable of providing an excellent deodorizing activity and is also excellent in the store stability.

13 Claims, No Drawings

(56) References Cited

OTHER PUBLICATIONS

Cho, S. W. et al.; "Halitosis inhibition against methyl mercaptan by polyphenol oxidase of apple extract," Session 104B, Fruit & Vegetable Products: Fruits (processed), 2003 Institute of Food Technologists Annual Meeting, retrieved from <www.internetarchive.org> as posted online Sep. 2003, p. 1 as provided.*

Negishi, Osamu et al.; "Enzymatic Deodorization with Raw Fruits, Vegetables and Mushrooms," Food Science and Technology Research, vol. 5, 1999, pp. 176-180.*

Negishi, Osamu et al.; "Deodorization with Ku-ding-cha Containing a Large Amount of Caffeoyl Quinic Acid Derivatives," 2004; ACS, Journal of Agriculture and Food Chemistry, vol. 52, No. 17, pp. 5513-5518.*

Lewis, Richard; "Hawley's Condensed Chemical Dictionary" 15$^{th}$ ed., 2007; entries for "bittern," "bleach," "brine," "lye," "metal," and "salt"; pp. 166, 168, 180, 772, 806 and 1105.*

WebElements Periodic Table of the Elements compounds for Aluminim, Copper, Magnesium, Manganese and Titanium, Retrieved from <www.webelements.com> on Mar. 7, 2012; pp. 1-15 as provided.*

Sigma Aldrich "Buffer Reference Center" retrieved from <www.sigmaaldrich.com> on Mar. 7, 2011, pp. 1-4.*

Cho, S. W. et al.; "Halitosis inhibition against methyl mercaptan by polyphenol oxidase of apple extract," Session 104B, Fruit & Vegetable Products: Fruits (processed), 2003 Institute of Food Technologists Annual Meeting, retrieved from as posted online Sep. 2003, p. 1 as provided.*

Burda, Stanislaw et al.; "Phenolic Compounds and Their Changes in Apples during Maturation and Cold Storage," 1990; ACS, Journal of Agriculture and Food Chemistry, vol. 38, No. 4, pp. 945-948.*

Oleszek, Wieslaw et al.; "Identification of Some Phenolic Compounds in Apples," 1988; ACS, Journal of Agriculture and Food Chemistry, vol. 36, No. 3, pp. 430-432.*

Jackson, Robert J. "Metal Salts, essential oils and phenols—old or new?", 1997, Munksgaard; Peridontology 2000 (ISSN 0906-6713), vol. 15, pp. 63-73.*

Hibino et al.; "Chemistry and Applications of Green Tea," Chapter 11 of: "Deodorizing Effects of Green Tea Extracts," 1997, CRC Press; pp. 123-127.*

Chinese Office Action issued in counterpart Chinese Application No. 2007800100065; dated May 11, 2010.

Negishi O., et al., "Effect of Polyphenol Oxidase on Deodorization", Bioscience Biotechnolgy Biochemistry, vol. 61, No. 12, XP000960678, Jun. 13, 1997, pp. 2080-2084.

Takezo Tanaka, et al., "Development trends of plant extracts with deodorizing effects and their application to air freshener and deodorizer", Fragrance Journal, No. 12, 1995, pp. 58-59.

Chinese Patent Office, Office Action issued in corresponding Chinese Application No. 200780010006.5 on Jul. 25, 2011.

Japanese Patent Office, Office Action dated Nov. 5, 2013 issued in counterpart Japanese Patent Application No. 2009501106.

Japanese Patent Office, Office Action dated Apr. 2, 2013, issued in counterpart Japanese Patent Application No. 2009-501106.

* cited by examiner

DEODORANT COMPOSITION

TECHNICAL FIELD

The present invention relates to a novel deodorant composition. That is, the invention relates to a novel deodorant composition comprising a polyphenol compound or a plant extract containing a polyphenol compound, or a granulated substance thereof; a basic substance; and a metal salt.

More specifically, the invention relates to a deodorant composition capable of providing a deodorizing effect in a short period of time when it is applied to a malodor source, providing an excellent deodorizing activity and also excellent in the store stability. Further, the invention relates to a novel deodorant composition used for elimination or reduction of malodors felt in daily life such as bad breath, odor in refrigerator, odor of raw garbage, odor of footwear cup board, body odor of human and animal, odor of feces and urine of human and animal odors, and malodors in factories and industrial liquid wastes.

BACKGROUND OF THE INVENTION

In recent years, with diversification of lives, improvement of life level, changes and improvement of attitudes, and the like, attention has been paid to various points around one's life. One of them is existence of various malodors. Main malodorous components include nitrogen compounds such as ammonia, urea, indole, skatole, and amines; sulfur compounds such as methyl mercaptan, hydrogen sulfide, and dimethyl sulfide; and lower fatty acids such as butyric acid. Heretofore, there are a number of reports on deodorants that are used to eliminate or reduce the malodors.

For example, there has been a report of using plant extracts containing various kinds of mixtures of polyphenols as detergents (refer to Patent Document 1). While such detergents show a certain level of deodorizing effect, most of them cannot be said to exhibit a sufficient deodorizing effect and, in this regard, leave a room for improvement.

As a deodorant which improves and solves the problem, it have been reported a deodorant composition comprising, as an effective component, a colored compound obtained by reacting a polyphenol compound in an alkaline solvent under the co-existence of oxygen molecules at a pH value during reaction of 6.5 or more has been reported (Patent Document 2). While the deodorant composition is an excellent deodorant composition capable of maintaining the deodorizing performance even with lapse of a long period of time when it is once prepared and capable of providing an excellent deodorizing effect to malodor component, particularly, to nitrogen-containing compound or sulfur-compound, since the effective ingredient is a colored substance, a problem has been pointed out that it undergoes a certain restriction upon application as a deodorant and cannot easily provide the deodorizing effect in a short period of time when it is applied to the malodor component.

Further, while a technique of preparing a deodorant composition comprising a polyphenol compound and an alkali has been reported (refer to Non-Patent Document 1), it is not intended to provide a deodorizing effect in a short period upon application to a malodor source.

Patent Document 1: JP-A-11-319051
Patent Document 2: JP-A-2004-167218
Non-Patent Document 1: Fragrance Journal No. 12, pages 58 to 59, 1995

DISCLOSURE OF THE INVENTION

In view of the above, the present invention intends to provide a novel deodorant composition capable of providing a deodorizing effect in a short period of time (within 20 minutes) when it is applied to a malodor source. In addition, the invention intends to provide a novel deodorant composition maintaining the features described above and scarcely undergoing the restriction when it is applied as a deodorant. Further, the invention intends to provide a novel deodorant composition capable of maintaining the features described above, excellent in the deodorizing effect, and capable of obtaining a deodorant composition by a simple method. Further, the invention also intends to provide a deodorant composition having an excellent deodorizing effect against malodor ingredient in a wide range.

In the course of earnest study for solving the subject described above, when a metal salt is added to a mixture of a polyphenol compound and an alkaline substance and the obtained mixture is applied to a malodor source, the present inventors have unexpectedly found that it starts to provide the deodorizing effect rapidly and can provide the deodorizing effect in a short period of time. They have made further earnest studies based on the finding, and finally they have accomplished the invention.

That is, the invention relates to the following (1) to (8).
(1) A deodorant composition comprising:
  (a) a polyphenol compound or a plant extract containing a polyphenol compound,
  (b) a basic substance, and
  (c) a metal salt.
(2) A deodorant composition comprising:
  (a) a granulated substance which contains a polyphenol compound or a plant extract containing a polyphenol compound,
  (b) a basic substance, and
  (c) a metal salt.
(3) The deodorant composition according to (1) or (2), which further comprises a polyphenol compound oxidase.
(4) The deodorant composition according to any one of (1) to (3), which further comprises a silicon dioxide.
(5) The deodorant composition according to any one of (1) or (4), wherein the basic substance is at least one member selected from the group consisting of brine, lye, and a bleach.
(6) The deodorant composition according to any one of (1) to (5), wherein the metal salt is bittern.
(7) A method for deodorizing a malodor, which comprises applying the deodorant composition according to any one of (1) to (6) to a malodor component.
(8) Use of the deodorant composition according to any one of (1) to (6) for deodorizing a malodor.

In this regard, the deodorant composition changes depending on the properly of the constituent ingredient, and it is sometimes colorless or white, pale gray, or gray, or sometimes has a pale color, for example, pale yellow, brown, etc. Further, it sometimes exhibits yellow color.

Namely, the invention provides a deodorant composition comprising (a) a polyphenol compound or a plant extract containing a polyphenol compound, (b) a basic substance, and (c) a metal salt as effective ingredients. Further, the invention can also be described as a deodorant composition consisting essentially of (a) a polyphenol compound or a plant extract containing a polyphenol compound, (b) a basic substance, and (c) a metal salt.

In the invention, the basic substance and the metal salt may be also used in the form of a granulated substance. While the ingredients described above are the essential ingredients in the inventions, other ingredients may also be present together so long as they do not impair the intended purpose.

The polyphenol compound oxidase may be an oxidase per se of the polyphenol compound, or a plant extract containing the oxidase.

According to the invention, a deodorant composition capable of exhibiting a deodorizing effect in a short period of time when applied to a malodor component can be provided. In addition, a deodorant composition exhibiting an excellent deodorizing activity and excellent in the store stability can be provided. Further, since the deodorant composition of the invention is colorless or exhibits white or pale color, it scarcely undergoes restriction upon application as the deodorant. The invention can provide a novel deodorant composition used for elimination or reduction of malodors felt in daily life such as bad breath, odor in refrigerators, odor of raw garbage, odor in footwear cup board, body odor of human and animal, odor of feces and urine of human and animal, and malodor in factories or industrial liquid wastes.

The present invention provides a deodorant composition exhibiting an excellent deodorizing effect on various malodor components. The deodorant composition of the invention is excellent in the deodorizing effect on malodor components, for example, sulfur-containing compounds such as methyl mercaptan, hydrogen sulfide, and dimethyl sulfide and lower fatty acids such as butyric acid and isovaleric acid among malodor components, and is also excellent in the deodorizing effect on amine malodor components such as ammonia which are alkaline. Furthermore, since the method for preparing the deodorant composition is relatively simple and it has an advantage that the deodorant performance is maintained even after the deodorant composition is stored for a long time once the deodorant composition is prepared, the composition can be said to be a remarkably excellent deodorant composition.

BEST MODE FOR CARRYING OUT THE INVENTION

The invention is to be described specifically.

At first, the polyphenol compound as the starting material for preparing the deodorant composition of the invention is to be described. The polyphenol compound used in the invention means a compound in which two or more hydrogen atoms on one identical benzene ring are substituted with hydroxyl groups, and glycosides thereof are also included as the polyphenol compound. The polyphenol compound used in the invention is not particularly restricted so long as it is a polyphenol compound capable of attaining the intended purpose. Among them, hydroquinone and a polyphenol compound having an o-diphenol structure are preferred. The o-diphenol structure means such a structure in which hydroxyl groups are directly substituted on the benzene ring and the hydroxyl groups are adjacent with each other.

Specific examples of the polyphenol compound include apigenin, apigenin glycosides, acacetin, isorhamnetin, isorhamnetin glycosides, isoquercitrin, epicatechin, epicatechin gallate, epigallocatechin, epigallocatechin gallate, aesculetin, ethyl protocatechuate salt, ellagic acid, catechol, γ-acid, catechin, gardenin, gallocatechin, caffeic acid, caffeic esters, chlorogenic acid, kaempferol, kaempferol glycosides, quercetin, quercetin glycosides, quercetagenin, genistin, genistin glycoside, gossypetin, gossypetin glycosides, gossypol, 4-dihydroxyanthraquinone, 1,4-dihydroxynaphthalene, cyanidin, cyanidin glycosides, sinensetin, diosmetin, diosmetin glycosides, 3,4'-diphenyldiol, sinapic acid, stearyl-β-(3,5-di-tert-butyl-4-hydroxyphenyl)propionate, spinacene, tangeritin, taxifolin, tannic acid, daphnetin, tyrosine, delphinidin, delphinidin glycosides, theaflavine, theaflavine monogallate, theaflavine bisgallate, tricetinidin, dopa, dopamine, naringenin, naringin, nordihydroguairetic acid, noradrenaline, hydroquinone, vanillin, patchouletin, herbacetin, vanillyl alcohol, vanitrope, vanillin propylene glycol acetal, vanillic acid, bis(4-hydroxyphenyl)sulfonic acid, bisphenol A, pyrocatechol, vitexin, 4,4'-biphenyldiol, 4-tert-butylcatechol, 2-tert-butylhydroquinone, protocatechuic acid, phloroglucinol, phenolic resins, procyanidin, prodelphinidin, phloretin, phloretin glycosides, fisetin, folin, fervasetin, fraxetin, phloridzin, paeonidin, paeonidin glycosides, pelargonidin, pelagugonidin glycosides, petunidin, petunidin glycosides, hesperetin, hesperidin, gallic acid, gallic esters (lauryl gallate, propyl gallate, butyl gallate), manjiferin, malvidin, malvidin glycosides, myricetin, myricetin glycosides, 2,2'-methylenebis(4-methyl-6-tert-butylphenol), 2,2'-methylenebis(4-ethyl-6-tert-butylphenol), 2,2'-methylenebis(4-methyl-6-tert-butylphenol), 2,2'-methylenebis(4-ethyl-6-tert-butylphenol), methyl atrarate, 4-methylcatechol, 5-methylcatechol, 4-methoxycatechol, 5-methoxycatechol, methylcatechol-4-carboxylic acid, 2-methylresorcinol, 5-methylresorcinol, morin, limocitrin, limocitrin glycosides, limocitrol, luteolin, luteolin glycosides, luteolinidin, luteolinidin glycosides, rutin, resorcin, resveratrol, resorcinol, leukocyanidin, leukodelphinidin.

Among these polyphenol compounds, preferred are flavonoids such as quercetin, epicatechin, and epigallocatechin and glycosides thereof; polyphenols having an o-diphenol structure, such as gallic acid, gallic esters, chlorogenic acid, caffeic acid, caffeic esters, tannic acid, pyrocatechol, nordihydroguairetic acid, L-dopa, 4-methylcatechol, 5-methylcatechol, 4-methoxycatechol, and 5-methoxycatechol; and hydroquinone.

The polyphenol compounds described above may be used each alone or as a mixture of two or more of them.

The above polyphenol compounds can be prepared by known methods but commercially available products may be purchased. Moreover, they may be prepared by synthesis. Furthermore, highly concentrated polyphenol fractions prepared from plants can be employed.

In the invention, instead of the polyphenol compound, a plant extract containing a polyphenol compound can also be used. As the plant extract, one prepared by a known method may be used or a commercially available product may be used.

Examples of the plant for the preparation of the plant extract containing a polyphenol compound include aloe, anise seeds, elder, eleutherococcus, psyllium, orange flower, allspice, oregano, valerian, chamomile, *capsicum* pepper, *cardamon, cassia*, garlic, caraway seeds, clove, cumin seeds, kola, coriander seeds, *Rhus javanica*, saffron, zanthoxylum, juniper berry, cinnamon, ginger, star anise, St. Johns wart, celery seed, savory, sesame, pieplant, tarragon, turmeric, thistle, *Anethum graveolens*, nutmeg, nettle, hibiscus, hamamelis, birch, basil, bitter orange, fennel, primrose, fenugreek, verbena, *Laurus nobilis*, hop, boldo, horseradish, poppy seed, gallnut, marigold, marrow, marjoram, mustard, Millefeuille, mint leaves, melissa, mace, lindane. Gentiana scabra var. *buergeri*, rosehip, rosemary, *Rosmarinus officinalis*, sunflower seeds, grape pericarp, apple, carrot leaves, banana, strawberry, apricot, peach, plum, pineapple, Nashi pear, persimmon, cherry, papaya, mango, avocado, melon, loquat, fig, kiwi, prune, blueberry, black berry, raspberry, cranberry, coffee beans, cacao beans, grape seeds, grape fruits seeds, pecan nut, cashew nut, chestnut, coconut, peanut, walnut, green tea leaves, black tea leaves, oolong tea leaves, tobacco, *perilla* leaves, garden thyme, sage, lavender, spearmint, peppermint, spotted thistle, hyssop, sweet basil, marigold, dandelion, artichoke, *Matricaria chamomille, Agrimonia pilosa* var.

*japonica*, licorice, anise, yarrow, eucalyptus, wormwood, balm, *Angelica pubescens*, fenugreek, *Capsicum annuum* var. *angulosum*, fennel, red pepper, coriander seeds, caraway seeds, fennel seeds, ginger, horseradish, *Origanum majorana, Origanum valgare*, mustard, parsley, pepper, savory, tarragon, queen lily, wasabi, dill seeds, citrus fruits, pear, thyme, and the like. Among them, rosemary, sunflower seeds, grape pericarp, apple, carrot leaves, banana, coffee beans, cacao beans, grape seeds, green tea leaves, black tea leaves, oolong tea leaves, *perilla* leaves, garden thyme, sage, spearmint, peppermint, pear and thyme are especially preferable.

The plant extract can be prepared from the plants each alone or in plurality. Further, individual plant extracts may be obtained and then such individual plant extracts may be mixed.

The preparation method of the plant extract is not particularly restricted.

Since the amount of the polyphenol compound to be used for obtaining the deodorant composition varies depending on the type of the malodor sources intended to be eliminated, the type and the amount of coexistent basic substance and the metal salt, etc., it cannot be defined generally, but it is about from 1 to 90% by weight and, more preferably, from 10 to 50% by weight based on the entire deodorant composition.

The basic substance (substance showing alkalinity) as the essential ingredient in the invention is a known chemical substance and not restricted particularly so long as it can attain the intended purpose of the invention. Specific basic substance includes, for example, carbonate salts or hydrogen carbonate salts such as sodium carbonate, potassium carbonate, sodium bicarbonate, ammonium carbonate, and guanidine carbonate; borate salts such as potassium borate and sodium borate; silicate salts such as potassium silicate, sodium silicate No. 1, sodium silicate No. 2, sodium silicate No. 3, sodium orthosilicate, and sodium metasilicate; sodium monohydrogen phosphate, sodium sulfite, sodium hydroxide, calcium hydroxide, potassium hydroxide, magnesium hydroxide, ammonium hydroxide, sodium pyrophosphate, and potassium pyrophosphate.

Further, the basic substance of the invention may also be at least one member selected from brine, lye and bleaches.

Brine has been used for noodle preparation for a long period of time. The main ingredient is sodium carbonate and potassium carbonate in which various other ingredients are present together. It is sold and is available easily.

Lye is a supernatant obtained mainly by dissolving and dispersing ashes of plant into water, which contains alkaline components such as potassium carbonate as a main ingredient. It is used for laundry agent or bleach. It is sold and available easily.

The bleach means a substance which chemically changes colored substances such as contaminants by oxidation or reduction into other substances, for which an oxygen type bleach or chlorine type bleach is often used. In the invention, oxygen type bleach is preferred.

Since the application of brine and lye in foods are allowed, they are preferably used in the deodorant composition for foods.

The basic substance may be used alone, or a plurality of basic substances may also be used.

Since the amount of the basic substance used for forming the deodorant composition varies depending on the type and the amount of the polyphenol compound used, the type and the amount of the metal salt, the malodor source to be deodorized, etc., it cannot be defined generally. A preferred result is obtained, for example, a in such a case that, when the deodorant composition of the invention is dissolved in water, pH of the aqueous solution thereof is 6.5 or more. Particularly, the aqueous solution preferably has pH of from 7 to 13, more preferably, pH of from 8 to 13, and still more preferably, pH of from 9 to 11. In a case where the pH of the aqueous solution is less than 6.5, a deodorant composition providing a preferred deodorizing effect cannot be obtained. On the other hand, in a case where pH is excessively high (pH at about 14), it needs caution upon handling the deodorant composition, which is disadvantageous.

The metal salt as the essential ingredient of the invention is not particularly restricted so long as it can attain the intended purpose. Among various metals salts, preferred metal salts are at least one or more metal salts selected from the group consisting of Mg salt, Ca salt, Cu salt, Mn salt, Ag salt, Ti salt, and Zn salt. Such metal salt are known chemical substances. Specific metal salt includes, for example, copper compounds such as copper chloride, copper fluoride, copper sulfate, copper nitrate, copper hydroxide, copper citrate, copper gluconate, copper aspartate, copper glutamate, sodium copper chlorophyllin and copper chlorophyll; zinc compounds such as zinc chloride, zinc fluoride, zinc sulfate, zinc nitrate, zinc hydroxide, zinc citrate, zinc gluconate, zinc aspartate, zinc glutamate, zinc phosphate, and zinc lactate; calcium compounds such as calcium chloride, calcium hydroxide, calcium citrate, calcium gluconate, calcium L-glutamate, calcium carbonate, calcium lactate, calcium pantothenate, calcium dihydrogen pyrophosphate, calcium propionate, calcium sulfate, tricalcium phosphate, calcium monohydrogen phosphate, calcium dihydrogen phosphate, and disodium calcium ethylenediamine tetraacetate; magnesium compounds such as magnesium chloride, magnesium sulfate, magnesium hydroxide, magnesium L-glutamate, magnesium oxide, and magnesium carbonate; silver compounds such as silver oxide; permanganate salts such as potassium permanganate and manganese compounds such as manganese sulfate, and the like. In addition, titanium compounds such as titanium dioxide can also be used.

In the invention, bittern can be used as the metal salt. Bittern is by produced upon preparation of table salts from sea water. It is sold and available easily.

Since the application of bittern in foods is allowed, it is preferably used in the deodorant composition for foods.

While the amount of the metal salt used varies depending on the polyphenol compound and the basic substance constituting the deodorant composition and the malodor source, it is preferably added such that the concentration of metal ions in the aqueous solution of the deodorant composition is from 0.00005 mM to 100 mM and it is, more preferably, from 0.0001 mM to 10 mM and, further preferably, from 0.01 mM to 5 mM.

The deodorant composition can also be prepared by putting the polyphenol compound or the plant extract containing a polyphenol compound to a granulating treatment and using the granulated substance thus obtained. The granulated substance may be a powder, granular powder, or capsule-like powder. Alternatively, it includes, for example, a powder with penetration and adsorption to a porous body, a powder encapsulated with natural gum or saccharides, a lock-in type powder sealed in a saccharide matrix, inclusion complex with cyclodextrin or the like, microcapsule coated with an external wall membrane containing an excipient, or powder prepared by using a roller compactor. Further, a powder of a larger diameter obtained, for example, by adsorption of such powder to each other is also the granulated substance of the invention.

In the invention, also the basic substance or the metal salt may be put to the granulating treatment and used as the constituent ingredient of the deodorant composition. Means for granulating the basic substance and the metal salt is not particularly restricted and means known so far may be adopted appropriately.

The powder with penetration and adsorption to a porous body is a powder obtained by penetration and adsorption of the polyphenol compound or the plant extract containing a polypyenol compound (hereinafter sometimes referred to as a polyphenol compound) to the porous body.

The porous body is not particularly restricted so long as it is a powder of an organic or inorganic compound capable of maintaining a powdery shape while carrying the polyphenol compound. Specifically, clay minerals such as calcium sulfate, calcium carbonate, diatomaceous earth, silicon dioxide, aluminum oxide, montmorillonite and kaolinite, inorganic compounds such as sodium chloride, low molecular weight organic compounds such as calcium lactate and lactose, starches such as dextrin, processed starch, and porous starch, cellulose derivatives such as crystalline cellulose, methyl cellulose, and cellulose ether compounds or organic compounds such as polyvinyl alcohol.

When an aqueous solution or dispersion of the polyphenol compound is used for the porous material and a known method is applied, a powder with penetration and adsorption to a porous body can be obtained. The grain size of the powder used is 0.5 mm or less and preferably, 100 µm or less.

The powder encapsulated with the natural gum or saccharide means a powder in which a polyphenol compound and the natural gum or saccharide are present together optionally with a surfactant and the polyphenol compound is encapsulated. Among them, particularly preferred encapsulated powder includes a powder in which the polyphenol compound is present together with the natural gum, optionally, a natural surfactant is present further together, and the polyphenol compound is encapsulated, or a powder in which the polyphenol compound is present together with the saccharide and, optionally, a natural surfactant and/or synthesis surfactant are present together, and the polyphenol compound is put to the encapsulating treatment.

The natural gum includes one or more members selected from processed starch, gum Arabic, soybean polysaccharides, etc. and the saccharides include one or more members selected from dextrin, starch, etc. Further, the natural surfactant includes one or more members selected from lecithin, saponin, quillai extract, quillai saponin, and the synthesis surfactant includes one or more members selected from sucrose fatty acid esters, polyglycerine esters, glycerine fatty acid esters, sorbitan fatty acid esters, and propylene fatty acid esters.

After mixing and stirring each of the ingredients, they are put to a powdering treatment. The powdering treatment referred to herein includes a spray drying treatment.

The powder sealed in the saccharide matrix means a powder in which the polyphenol compound is sealed in the matrix material. The saccharide includes, for example, monosaccharides, disaccharides, polysaccharides, sugar alcohols, polyols, saccharide derivatives, processed starch, modified starch and gums. More specifically, they include, for example, sucrose, glucose, lactose, levurose fluctose, maltose, glucopyranosyl mannitol, glucopyranosyl sorbitol, ribose, dextrose, isomalt, sorbitol, mannitol, xyrol, lactitol, maltitol, pentatol, arabinose, pentose, xylose, gallactose, starch, hydrogenated starch hydrolyzate, maltodexctrin, agar, carrageenan, polydextrose, as well as derivatives and mixtures thereof.

The manufacturing method of the powder is as described below. At first, water is added optionally to the matrix material and heated to form a molten product of the matrix material. Then, polyphenols are added to the obtained molten product and mixed and stirred while heating to obtain a highly viscous liquid mixture, which is subsequently extruded by an extruder into a solvent to obtain a powder.

The clathrate body means a compound formed from a basket-like clathrate lattice prepared with host molecules and intaking (including) a polyphenol compound in the space thereof. While the host molecule is not particularly restricted, cyclodextrin is a typical host molecule. The cyclodextrin used herein includes one or more of α-cyclodextrin, β-cyclodextrin, and γ-cyclodextrin, as well as derivatives formed by α-1,6-bonding of one molecule or two molecules of saccharides such as glucose, maltose, and malto-triose, cyclodextrin derivatives in which at least a portion of the glucose residue is chemically modified with a hydrophilic functional group such as hydroxyethyl, 2-hydroxypropyl, 2,3-dihydroxypropyl, 2-hydroxybutyl, 2-hydroxyisobutyl, diethylaminoethyl, and trimethyl ammoniopropyl, cyclodextrin polymers polymerized by a crosslinker such as epichlorohydrin or polyvalent glycidyl ether, and cyclodextrin derivatives selected from branched cyclodextrins having branched side chains such as glucose or maltose.

While the clathrate body is obtained by stirring and mixing cyclodextrins or a cyclodextrin derivative and a polyphenol compound under the presence of water, followed by filtering and drying the precipitated clathrate compound, or prepared by using the same as an aqueous solution as it is, or further optionally drying and powdering the clathrate compound, the invention is not restricted at all to such methods.

The powder prepared by using the roller compactor is a powder prepared from a composition containing a polyphenol compound, and an excipient by using a roller compactor. As the excipient, hydrophilic substance is preferred and hydrophilic proteins such as gelatin, casein, sodium casein, whey protein, defat powdered milk, whole fat powdered milk, and albumin, hydrophilic polysaccharides such as malto-dextrin, processed starch (acid-decomposed starch, oxidized starch, alpharized starch, grafted starch, etherified starch, esterified starch formed by reacting with acetic acid, phosphoric acid, etc.), hydrophilic polysaccharides such as alginate salts, gum Arabic, soybean polysaccharide, guar gum, xanthan gum, pectin, carboxymethyl cellulose, and agarose, partially hydrolyzed proteins such as HAP, HVP, partially decomposed starch such as oligo-saccharide, and saccharides typically represented by lactose.

While description has been made mainly for the powder, granules or capsules are also included in the invention. For example, granules prepared by using the roller compactor, granulated substances in which powders obtained by further treating powders to each other are adsorbed each other are also included in the granulated substances referred to in the invention. Further, granulated substances obtained by applying a coating treatment with oils and the fats or cellulose to the powder described above are also included in the granulated substance referred to in the invention. Further, granulated substances obtained by a double coating treatment are also included in the granulated substance referred to in the invention.

As the constituent ingredient for the deodorant composition of the invention, silicon dioxide may further be used. As a mode of using silicon dioxide, silicon dioxide may be added to a mixture of the ingredient (a), the ingredient (b), and the ingredient (c), it may also be used being added to one of the ingredients described above.

The deodorant composition containing silicon dioxide has an advantage that the handlability is improved upon application to the malodor source or upon preservation. In addition, this is also effective to the improvement of the store stability of the deodorant composition.

The deodorant composition of the invention can be prepared by mixing (a) the polyphenol compound or the plant extract containing a polyphenol compound, (b) the basic substance, and (c) the metal salt. Each of the ingredient can be stored separately and each of the ingredients may be mixed when it is intended to provide the deodorizing effect. Accordingly, the invention also includes a case of separately storing each of the ingredients constituting the deororant composition of the invention. For example, a mixture of the ingredient (a) and the ingredient (c), and the ingredient (b) may be considered as the deodorant composition of the invention, and a mixture of the ingredient (b) and the ingredient (c), and the ingredient (a) can be considered to be as the deodorant composition. Further, a case in which the ingredient (a) and the ingredient (b) and the ingredient (c) are stored separately can also be considered as the deodorant composition of the invention.

In the invention, each of the ingredients may be mixed with the solvent into a liquid product. The solvent includes, for example, water, hydrous alcohol, lower alcohol (methanol, ethanol, butanol, propanol, etc.), polyol type organic solvent (ethylene glycol, propylene glycol, etc.), benzyl alcohol, glycerol, monoglyceride, diglyceride, animal and plant oils, essential oils, etc.

Further, each of the ingredients can be used in a state of a solid product or a gelled product. While a preferred solid product can include a powder, the powder has already been described above.

The microcapsule coated with an external wall membrane comprising the excipient means a powder obtained by coating the polyphenol compound with the excipient.

As the example of the gelled substance, gelled powder obtained by causing each of the ingredients to be present together with the gelling agent is preferred. The gelling agent include aqueous gelling agents such as carrageenin, carboxyvinyl polymers, crosslinked polyacrylic acids, hydroxyethyl cellulose, carboxymethyl cellulose, sodium acrylate, agar, gelatin, pectin, furcellaran, xanthan gum, locust bean gum, gellan gum, and collagen; oily gelling agents such as metal soaps and dibenzylidene sorbitol. They can be used each alone or in combination.

The deodorant composition of the invention can also be supported on carrier. As a method for supporting the deodorant composition of the invention on the carrier, there can be mentioned a method of forming a deodorant composition in a solution state, depositing the same to the support by means of coating, impregnation, spraying, or the like and subsequently drying the same (e.g., air-drying at 60° C. for 12 hours), as an example.

The deodorant composition of the invention can be supplied on an optional carrier and, in addition, may be used after capsulation by a known method using gelatin, gum arabic, sodium arginate, a cellulose derivative such as ethyl cellulose, polyvinyl alcohol, vinyl methyl ether-maleic anhydride copolymer, styrene-maleic anhydride copolymer, polyethylene, polystyrene, paraffin wax or the like.

In the invention, commercially available various additives can be added to the deodorant composition obtained by the method described above. Examples of the additives include extenders, antioxidants, dyestuffs, known deodorizing materials, enzymes for reducing malodor, surfactants, fragrances and flavors, stabilizers, antibacterial agents, moisture absorbents (calcium chloride, highly water-absorbable polymers, etc.), excipients (lactose, etc.), and the like.

They can be blended with the deodorant composition of the invention each alone or as a combination of two or more of them and thus a characteristic deodorant can be prepared. Particularly, when the antibacterial agent is blended with the deodorant composition, the deodorizing effect is synergistically enhanced and, accordingly it becomes possible to prepare a more characteristic deodorant by combining the antibacterial agent with other additives to develop the performances of the additives. The mixing amount of the additives is not particularly limited so far as the amount can accomplish the desired purpose.

The extender includes saccharides, polysaccharides, the processed starch, casein, gelatin, carboxymethyl cellulose (hereinafter referred to as CMC), lecithin, and the like.

As the antioxidant, there are known butylhydroxy toluene, butylhydroxy anisole, citric acid, biofavoic acid, glutathione, selenium, licopene, vitamin A, vitamin E, and vitamin C, as well as pyrrolopyrrole derivatives, free radical scavengers obtainable from extracts of various plants, enzymes having antioxidant properties such as superoxide dismutases and glutathione peroxidases, and the like.

As the dyestuffs, dyes, lakes, organic synthetic dyestuffs (tar dyestuffs) such as organic pigments, natural dyestuffs, inorganic pigments, and the like can be employed. Specifically, examples thereof include hibiscus dyestuff, huckleberry dyestuff, plume dyestuff, layer dyestuff, duberry dyestuff, grape juice dyestuff, blackberry dyestuff, blueberry dyestuff, mulberry dyestuff, morello cherry dyestuff, red currant dyestuff, loganberry dyestuff, paplica powder, malt extract, rutin, flavonoids, red cabbage dyestuff, red radish dyestuff, adzuki bean dyestuff, turmeric dyestuff, olive tea, cowberry dyestuff, *chlorella* dyestuff, saffron dyestuff, *perilla* dyestuff, strawberry dyestuff, chicory dyestuff, pecannut dyestuff, red rice malt dyestuff, safilower dyestuff, purple sweet potato dyestuff, lac dyestuff, spirulina dyestuff, onion dyestuff, tamarind dyestuff, chili pepper dyestuff, gardenia dyestuff, Gardenia jasminoides dyestuff, sikon dyestuff, rosewood dyestuff, euphausiid dyestuff, orange dyestuff, carrot carotene, carmel, sodium iron chlorophyllin, riboflavin, norbixin potassium, norbixin sodium, alamance, erythrocin, new coccin, phloxine B, rose bengal, acid red, cutoradin, sunset yellow, first green, brilliant blue, indigocarmine, lake red C, lithol red, rhodamine, phloxine, indigo, ponceau, orange I, and sudan blue. Further, inorganic pigments include mica, talc, calcium carbonate, kaolin, silicic anhydride, aluminum oxide, colcothar, iron oxide, ultramarine, carbon black, titanium dioxide, zinc oxide, mica, bismuth oxychloride, boron nitride, photochromic pigments, hybrid fine powder, and synthetic mica.

The antibacterial agents include benzoic acid, sodium benzoate, isopropyl p-hydroxybenzoate, isobutyl p-hydroxybenzoate, ethyl p-hydroxybenzoate, methyl p-hydroxybenzoate, butyl p-hydroxybeazoate, propyl p-hydroxybenzoate, sodium sulfite, sodium hyposulfite, potassium pyrosulfite, sorbic acid, potassium sorbate, sodium dehydroacetate, thujaplicin, udo extract, storax extract, wild tansy extract, milt protein extract, and zymolytic Yokuinin extract.

Known deodorants include, for example, deodorants due to the desulfurizing action of iron sulfates such as ferrous sulfate and iron chlorides; deodorants due to the chemical reaction of acidic agents, alkaline agents, oxidizing agents, and the like; deodorants due to the adding or condensing action of (meth) acrylate esters, maleate esters, and the like as adding agents or glyoxal as a condensing agent; deodorants due to the ion-exchanging action of amphoteric ion-exchange resins, cationic ion-exchange resins, anionic ion-exchange resins, and the like; deodorants due to the chemical attaching or adsorbing action of alkaline or acidic attaching active carbon, mixtures of active carbon and a chemical reagent; deodorants due to the adsorbing action of porous adsorbents such as neutral active carbon, fibrillated carbon deodorant, zeolite, and active white clay; deodorants due to the enzymatic action of digestive enzymes or enzymes produced by mouth good bacterium LS-1 lactic acid bacterium, yeasts, soil bacteria, and the like or bacteria per se, deodorants due to the antiseptic or bactericidal action of chloramine T, parabens, phenols, and the like; polyphenol compound deodorants such as persimmon polyphenol, tea chatechin, rosemary extract, oolong tea extract, tansy extract, white oak leave extract, and rice bran/soy bean-roasted extract; and the like. In addition, they also include cyclodextrin, champignon extract, rooibos extract, sodium iron chlorophyllin, active carbon, zeolite, and the like.

In the deodorant composition of the invention, a polyphenol compound oxidase may be present together. Preferred enzymes include catechol oxidase, polyphenol oxidase, tyrosinase, laccase, peroxydase, and the like. For the deodorant composition in the invention, an enzyme exhibiting an enzymatic activity in an alkaline region is used particularly preferably.

While the addition amount of the enzyme is not particularly restricted, it is preferably added in such an amount that the enzymatic activity is 100 unit or more per 100 g of the polyphenol compound of the deodorant composition. For the unit of the enzymatic activity referred to herein, it is defined as 1 unit when the absorption value at OD of 265 nm is increased by 0.001 in a case of reaction for 1 min under the condition at a pH value of 6.5 and at a temperature of 25° C. using (L)-DOPA (L-DOPA) as a substrate.

In the invention, crude enzymes obtained from extracts of the plants (hereinafter sometimes referred to as a plant-derived enzyme powder) can also be used. The crude enzymes are not restricted particularly so long as the intended purpose of the invention is not impaired. Specific plants for preparing the crude enzymes include mashrooms of agarics and boretus gene, apple, banana, Nashi pear, pear, strawberry, persimmon, pineapple, grape, apricot, peach, plum, papaya, quince, avocado, mango, cherry, apricot, melon, loquat, fig, prune, kiwi, blue berry, black berry, raspberry, cranberry, currant, burdock, egg plant, tomato, mugwort, lotus root, lettuce, cabbage, sugar beat, hop, parsnip, spinach, radish, turnips, cauliflower, chicory, onion, celery, carrot, asparagus, horse radish, ginger, aloe, green pepper, barley, wheat, corn, alfalpha, malt, broad bean, soybean, azuki bean, runner bean, *vigna radiate*, potato, sweet potato, sweet corn, dasheen, tea, tobacco, olive, nutmeg and chrysanthemum. Among them, mashrooms of agarics and boretus gene, apple, banana, Nashi pear, pear, burdock, horse radish, tea and tobacco are especially preferable. Freeze dried powder obtained by freeze-drying the plants, and hot blow dried powder obtained by hot blow-drying them are also included in the enzyme of the invention, Further, acetone powder obtained from the plants are also included in the enzyme of the invention.

The surfactants include nonionic type (polyoxyethylene alkyl ethers, fatty acid alkylolamides, etc.), acylglutamic acid type, and the like. The surfactants are preferably used each alone or as a combination of two or more of them. Examples of the polyoxyethylene alkyl ethers include polyoxyethylene stearyl, polyoxyethylene hardened castor oil, and the like. Examples of the fatty acid alkylolamides include coconut-oil fatty acid diethanolamide. The acylglutamic acid type includes glutamate esters of saturated and unsaturated fatty acids having 12 to 18 carbon atoms, and coconut-oil fatty acids, hardened coconut-oil fatty acids, palm-oil fatty acids, hardened palm oil fatty acids, beef-tallow fatty acids, hardened beef-tallow fatty acids, and the like which are mixtures the saturated and unsaturated fatty acids having 12 to 18 carbon atoms and, specifically, it includes N-coconut-oil fatty acid-acyl-L-glutamic triethanolamine, lauroyl-L-glutamic triethanolamine, sodium N-coconut-oil fatty acid-acyl-L-glutamate, sodium N-lauroyl-L-glutamate, sodium N-myristoyl-L-glutamate, sodium N-coconut-oil fatty acid-hardened tallow fatty acid-acyl-L-glutamate, potassium N-coconut-oil fatty acid-acyl-L-glutamate, and the like.

For the deodorant compositions, flavors and/or fragrances (hereinafter sometimes referred to as perfumes) may be used. As a result, strange odors characteristic to substrates can be masked and further pleasant aroma can be also imparted.

Any of the perfumes may be used with no particular restriction which may be either synthesis perfumes or natural essential oils and may be in any of liquid, paste or solid states. For example, the flavors used in the invention include synthetic perfumes such as esters, alcohols, aldehydes, ketones, acetals, phenols, ethers, lactones, furans, hydrocarbons and acids, as well as natural perfumes.

The fragrance used in the invention include hydrocarbons, alcohols, phenols, aldehydes, and/or acetals, ketones and/or ketals, ethers, synthetic musks, acids, lactones, esters, halogen-containing compounds, and natural perfumes.

Further, in addition to the flavors and fragrance described above, perfumes describes, for example, in "Nihon ni Okeru Syokuhin Kouryou Kagoubutu no Shiyou Jittai Tyousa (Investigation for the Actual Use of Food and Perfume Compounds in Japan)" (Welfare and Science Research Report in Hei 12 (2000): published from Nippon Perfume Industry Association, March, Hei 13 (2001), "Gousei Kouryou, Kagaku to Syouhin Chishiki, (Synthetic Perfumes, Chemistry and Merchandise Knowledge)" (written by Motoichi Indoh, published Mar. 6, 1996, from The Chemical Daily Co., Ltd.), and "Perfume and Flavor Chemicals (Aroma Chemicals) 1,2" (Steffen Arctender (1969)) can be used.

The flavors and the fragrances may be used each alone or two or more of them in admixture.

Commercial products may be used for them. Further, for the single component products, synthesis products may be used or they may be introduced from natural origin such as plants. Essential oils, resinoids, balsams, absolutes, concretes, tinctures may be prepared by known methods and used.

Specific examples of the perfume ingredient include hydrocarbons perfumes such as limonene, pinen, γ-terepinen, and caryophyllene; alcohol perfumes such as phenyl ethyl alcohol, terepineol, bacdanol, geraniol, nerol, linarol, and cis-3-hexenol; aldehyde perfumes such as lilial, citral, aldehyde C-8, aldehyde C-9, aldehyde C-11, hexyl cynnamic aldehyde, vanillin, and heliotropin; keton perfumes such as yonon, rosephenone, woody flow, damasnin, isoe super; other perfume such as musks, eugenol and coumarin, in which compounds containing no sulfur or nitrogen atom are especially preferable; essential oils such as lemon oil, orange oil, and peppermint oil; and essences such as apple essence and strawberry essence. In the invention, one or more of the perfume ingredients are contained.

Further, together with the perfumes, solvent (ethanol, ethylene glycol, propylene glycol, diethylene glycol, etc.), emulsifiers, solubilizers, retainers, perfume retainers, cooling agents, warming agents, enhancers, anti-oxidants and photo-degradation inhibitors can also be used properly (refer, for example, to "Syuuchi Kanyou Gijyutsusyu (Kouryou) Dai-ichibu, Kouryou Ippan, (well-known customary technical collection (perfume) Part 1 Perfume general)" published from Japan Patent Office, on Jan. 29, 1999).

While the blending amount of the perfume varies depending on the polyphenol compound used, the object to which the deodorant composition is applied, method of use, etc., it is usually preferred to be from 0.001 to 10% by weight based on the deodorant composition.

The deodorant composition of the invention is effective for elimination or reduction of a wide range of malodors.

Specifically, it is effective for elimination or reduction of various odors including odors felt in daily life, such as bad breath, odor in refrigerator, odor of feces and urine of human, animals, and birds, body odor, and odor of raw garbage, and malodors in factories and industrial liquid wastes.

Further, the deodorant composition of the invention is excellent in the deodorizing effect on sulfur-containing compounds such as methyl mercaptan, hydrogen sulfide, and dimethyl sulfide; nitrogen compounds such as ammonia, urea, indole, skatole, and amines; and lower fatty acids such as butyric acid. Among them, the deodorant composition of the invention is particularly excellent in the deodorizing effect on sulfur-containing compounds such as methyl mercaptan, hydrogen sulfide, and dimethyl sulfide.

Further, the deodorant composition of the invention can be incorporated into the following products or goods to exhibit the deodorizing performance. Specifically, products or goods include drinks such as various drinks and powdery drinks; foods such as jellies, tablet sweets, munches, processed seafoods, processed meat products, seasonings, powdery foods including powdery soups and powdery desserts, baked munches, retort foods, frozen foods, instant noodles, healthy foods, foods for microwave oven cooking, various confectionary products, and various desserts; oral care products such as mouthwash, toothpaste, chewing gum, tablets, hard candy, soft candy, capsules, and oral spray; articles for pets animals including dog, cat, rabbit, hamster, and parakeet, such as cat sands, cat sleeping straws, and sheets; detergents such as laundry detergents, kitchen detergents, bathroom detergents, carpet detergents, and toilet detergents; cosmetics such as soaps, body shampoos, hand soaps, lotions, face lotion, antiperspirants, foot deodorant sprays, and foot powders; hair care products such as shampoos, conditioners, hair rinses, hair coloring agents, permanent-wave agents, waxes, hair sprays, and mousse; bath agents; sanitary goods such as paper diapers, paper pads, sanitary napkins, sheets, towels, and wet tissues; household cleaning products, footwear cupboard sprays, sheets in shoes, raw garbage sprays, filters for air cleaners and air conditioners, deodorizers, air blowers and air dischargers, deodorants for refrigerators, deodorants for cloths, deodorant for drawers, closets, and ambries, room or car deodorants, toilet deodorants, deodorants for textile products, cloths (underwear and socks), car sheets, deodorant fibers, deodorants for factories and industrial liquid wastes and other various deodorants.

While the amount of use of the deodorant composition of the invention varies depending on the kind and the form of the products or commercial goods, it is generally within a range about from 0.001 to 0.1 parts by weight and, preferably, about from 0.01 to 0.05 parts by weight based on one part by weight of the products or commercial goods.

At deodorization of malodor using the deodorant composition of the invention, a conventional method can be applied. For example, when a solid matter, gel matter, or liquid matter of the deodorant composition of the invention is applied by a method of directly scattering, sprinkling, wiping, immersing, or placing the composition to the site or place where a malodor component is present or the site or place where possible generation of a malodor component may be predicted, it is possible to eliminate the malodor component or prevent the generation thereof. Further, the deodorant composition of the invention may be applied by a spraying method.

EXAMPLE

The present invention is to be described specifically by way of examples but the invention is no way restricted to them.

Examples 1 to 5

Preparation of Deodorant Composition

2 µmol of chlorogenic acid, 100 µmol of sodium hydrogen carbonate, and 0.5 µmol of a metal salt described in Table 1 were admixed to obtain a deodorant composition.

Test Example 1

Deodorizing effect of deodorant composition on methyl mercaptan

Deodorant composition of Examples 1, 2 mL of water, and 4 µL of an aqueous 15% solution of sodium methyl mercaptan (manufactured by Tokyo Chemical Industry Co., Ltd.) were added to a 50 mL vial bottle, which was covered with a para-film and stirred at 25° C. In a predetermined time, 50 µL of a head space gas in the vial bottle was passed through a gas detection tube (manufactured by GASTEC Corporation), the concentration of the contained sulfur compound as a malodor component remained in the gas was measured and the deodorizing ratio was calculated in accordance with the following equation. The results are shown in Table 1.

Deodorization ratio (%)=100×{1−(A/B)}

In the formula, A represents the measured concentration of the malodor component, and B represents the concentration of the malodor component measured as a control.

In the control, 2 mL of water was added to 100 µmol of sodium hydrogen carbonate.

Comparative Example 1

2 µmol of chlorogenic acid and 100 µmol of sodium hydrogen carbonate were mixed to obtain a deodorant composition of Comparative Example 1.

Comparative Example 2

After adding 50 mL of water to a mixture of 1 mmol of chlorogenic acid and 50 mmol of sodium hydrogen carbonate and stirring at a room temperature for three hours under the condition capable of being in contact with oxygen, they were freeze-dried to obtain a colored compound, and 12 mg of which was used as a deodorant composition of Comparative Example 2.

Comparative Example 3

50 mL of water was added to a mixture of 1 mmol of chlorogenic acid, 50 mmol of sodium hydrogen carbonate, and 0.25 mmol of magnesium chloride and the same procedures as those in Comparative Example 2 were conducted subsequently to obtain a colored compound, and 12 mg of which was used as a deodorant composition of Comparative Example 3.

Test Example 2

The deodorizing effect of the deodorant compositions of Examples 2 to 5 on methyl mercaptan was measured in accordance with the same procedures as those in Test Example 1.

The results of measurement are shown in the following Table 1.

Test Example 3

The deodorizing effect of the comparative deodorant compositions of Comparative Examples 1 to 3 on methyl mercaptan was measured in accordance with the same procedures as those in Test Example 1.

The results of measurement are shown in the following Table 1.

TABLE 1

| | Metal salt | Deodorizing time | | | | |
|---|---|---|---|---|---|---|
| | | 0 min | 5 min | 10 min | 20 min | 30 min |
| Comp. Example 1 | Not added | 0.0 | 0.0 | 0.0 | 15.0 | 20.0 |
| Example 1 | +magnesium chloride | 0.0 | 35.0 | 55.0 | 100.0 | 100.0 |
| Example 2 | +calcium chloride | 0.0 | 30.0 | 50.0 | 95.0 | 100.0 |
| Example 3 | +copper chloride | 0.0 | 70.0 | 100.0 | 100.0 | 100.0 |
| Example 4 | +zinc chloride | 0.0 | 40.0 | 70.0 | 100.0 | 100.0 |
| Example 5 | +manganese sulfate | 0.0 | 80.0 | 100.0 | 100.0 | 100.0 |
| Comp. Example 2 | not added | 0.0 | 0.0 | 25.0 | 45.0 | 70.0 |
| Comp. Example 3 | magnesium chloride contained | 0.0 | 5.0 | 30.0 | 60.0 | 75.0 |

Examples 6 to 9

Preparation of Deodorant Composition

2 μmol of chlorogenic acid, 100 μmol of sodium hydrogen carbonate, 0.5 μmol of metal salt described in Table 2, and 10 mg of enzyme powder derived from plants described in Table 2 were added and mixed to obtain a deodorant compositions.

Test Example 4

The deodorizing effect of the deodorant compositions of Examples 6 to 9 on methyl mercaptan was measured in accordance with the same procedures as those in Test Example 1.

The results of measurement are shown in the following Table 2.

TABLE 2

| | Metal salt + plant derived Enzyme powder | Deodorizing time | | | | |
|---|---|---|---|---|---|---|
| | | 0 min | 5 min | 10 min | 20 min | 30 min |
| Example 6 | +magnesium chloride + burdock acetone powder | 0.0 | 65.0 | 95.0 | 100.0 | 100.0 |
| Example 7 | +calcium chloride + pear freeze-dried powder | 0.0 | 50.0 | 70.0 | 100.0 | 100.0 |
| Example 8 | +copper chloride + apple freeze-dried powder | 0.0 | 100.0 | 100.0 | 100.0 | 100.0 |
| Example 9 | +zinc chloride + banana freeze-dried powder | 0.0 | 70.0 | 95.0 | 100.0 | 100.0 |

According to Table 1 and Table 2, by mixing a predetermined metal salt to the system of the polyphenol compound and basic substance, the deodorizing effect was improved remarkably more than the system of the polyphenol compound and the basic substance. It shows more excellent effect even when compared with the colored compound formed with an identical starting material composition.

It was further found that the deodorizing effect was improved further in a case where a polyphenol oxidase operating also in an alkaline region of pH 7 or higher was present together.

It was further found that the deodoring effect was improved further in a case where a polyphenol oxidase operating also in an alkaline region of pH 7 or higher was present together.

For the burdock acetone powder in the table, 400 liter of acetone at −20° C. was added to 100 g of the plant, ground in a mixer and then filtered under suction. The residue was washed sufficiently with 500 ml of an aqueous 80% acetone-containing solution at 5° C. and, after joining with filtrates and distilling off acetone, it was freeze-dried into a powder.

Further, pear freeze-dried powder, apple freeze-dried powder, and banana freeze-dried powder were prepared by slicing each of the plant, then freeze-drying and then pulverizing the same.

Examples 10 to 18

Preparation of Deodorant Composition

2 μmol of polyphenol compounds, 100 μmol of basic substances and 0.5 μmol of metal salts each described in Table 3 were added and mixed to obtain deodorant compositions.

Test Example 5

The deodorizing effect of deodorant compositions of Examples 10 to 17 on methyl mercaptan was measured in accordance with the same procedures as in the test example 1.

Results of measurement are shown in the following Table 3.

Comparative Examples 4 to 12

2 μmol of the polyphenol compounds and 100 μmol of the basic substances each described in Table 3 were mixed to obtain comparative deodorant compositions.

Test Example 6

The deodorizing effect of deodorant compositions of Comparative Examples 4 to 11 on methyl mercaptan was measured in accordance with the same procedures as in Test Example 1.

Results of measurement are shown in the following Table 3.

TABLE 3

|  | Polyphenol compound | Basic substance | Metals salt |
|---|---|---|---|
| Comp. Example 4 | Gallic acid | Bleacher | — |
| Example 10 | Gallic acid | Bleacher | magnesium chloride |
| Comp. Example 5 | (+)-catechin | Sodium hydroxide | — |
| Example 11 | (+)-catechin | Sodium hydroxide | magnesium chloride |
| Comp. Example 6 | α G rutin | Lye | — |
| Example 12 | α G rutin | Lye | magnesium chloride |
| Comp. Example 7 | Caffeic acid | brine | — |
| Example 13 | Caffeic acid | brine | magnesium chloride |
| Comp. Example 8 | green tee extract | sodium hydrogen carbonate | — |
| Example 14 | green tee extract | sodium hydrogen carbonate | magnesium chloride |
| Comp. Example 9 | Coffee raw bean extract | sodium hydroxide | — |
| Example 15 | Coffee raw bean extract | sodium hydroxide | magnesium chloride |
| Comp. Example 10 | Apple extract | sodium hydroxide | — |
| Example 16 | Apple extract | sodium hydroxide | magnesium chloride |
| Comp. Example 11 | Grape pericarp extract | sodium hydrogen carbonate | — |
| Example 17 | Grape pericarp extract | sodium hydrogen carbonate | bittern |
| Comp. Example 12 | Peppermint extract | brine | — |
| Example 18 | Peppermint extract | brine | bittern |

|  | Deodorizing time | | | | |
|---|---|---|---|---|---|
|  | 0 min | 5 min | 10 min | 20 min | 30 min |
| Comp. Example 4 | 0.0 | 0.0 | 10.0 | 15.0 | 20.0 |
| Example 10 | 0.0 | 50.0 | 70.0 | 100.0 | 100.0 |
| Comp. Example 5 | 0.0 | 0.0 | 0.0 | 10.0 | 20.0 |
| Example 11 | 0.0 | 30.0 | 60.0 | 100.0 | 100.0 |
| Comp. Example 6 | 0.0 | 0.0 | 0.0 | 10.0 | 15.0 |
| Example 12 | 0.0 | 30.0 | 50.0 | 85.0 | 100.0 |
| Comp. Example 7 | 0.0 | 0.0 | 0.0 | 0.0 | 10.0 |
| Example 13 | 0.0 | 35.0 | 50.0 | 95.0 | 100.0 |
| Comp. Example 8 | 0.0 | 0.0 | 10.0 | 20.0 | 35.0 |
| Example 14 | 0.0 | 60.0 | 95.0 | 100.0 | 100.0 |
| Comp. Example 9 | 0.0 | 0.0 | 5.0 | 15.0 | 30.0 |
| Example 15 | 0.0 | 50.0 | 80.0 | 100.0 | 100.0 |
| Comp. Example 10 | 0.0 | 0.0 | 1.0 | 20.0 | 30.0 |
| Example 16 | 0.0 | 50.0 | 85.0 | 100.0 | 100.0 |
| Comp. Example 11 | 0.0 | 0.0 | 5.0 | 10.0 | 30.0 |
| Example 17 | 0.0 | 40.0 | 70.0 | 95.0 | 100.0 |
| Comp. Example 12 | 0.0 | 0.0 | 5.0 | 15.0 | 30.0 |
| Example 18 | 0.0 | 50.0 | 80.0 | 100.0 | 100.0 |

In Table 3, bleach, lye, brine, and bittern are commercial products.

Extracts Referred in Table 3:

Green Tea Extract:

1 Kg of boiled tea was extracted under stirring with 10 L of hot water at 90° C. for one hour and tea leaves were removed by filtration to obtain 8.3 L of extract. The solution was concentrated to 1 L, to which 1 L of acetone was added and stirred, and resultant insoluble matters were removed by centrifugation. 1 L of ethyl acetate was added to the supernatant and stirred and stood still for 30 min. The obtained ethyl acetate layer was concentrated under a reduced pressure, transformed into an aqueous layer, and then freeze-dried to obtain 97 g of green tea extract at 60% purity.

Coffee Raw Bean Extract:

After pulverizing coffee raw bean by a pulverizer (5 mm mesh), water was added to extract at 85 to 95° C. for 2 hours. After filtration of extracts, filtrate was adsorbed to an XAD-2 column (manufactured by Organo Corp.). After washing with water and leached with ethanol, it was concentrated and dried to solid to form coffee raw bean extract.

Apple Extract:

Manufactured by Nikka Whisky Co.

Grape Pericarp Extract:

After adding ethanol to grape pericarp (variety: Campbell), it was stirred and extracted at 70° C. for 2 hours. The extract which was concentrated and dried to solid was used as a grape pericarp extract.

From the results shown in Table 3, it was found that by mixing a predetermined metal salt to the system of the polyphenol compound and the basic substance, the deodorizing effect was remarkably improved more than that in the system of the polyphenol compound and the basic substance.

Example 19

Preparation of Deodorant Composition

The following polyphenol compound-containing granulated substance was prepared, the granulated substance was weighed by such an amount that the polyphenol compound content was 2 μmol, and then 100 μmol of sodium hydrogen carbonate and 0.5 μmol of magnesium chloride were added and mixed to obtain a deodorant composition.

Preparation of Polyphenol Compound-Containing Granulated Substance

While stirring together with 10 parts by weight of catechin (polyphenol powder GTP90: manufactured by Aiya Co.) dispersed in 27 mL of ion exchanged water, 66.79 parts by weight of isomalt (palatinit), 0.95 parts by weight of processed starch (purity gum 59: manufactured by National Starch and Chemicals Co.), and 22.26 parts by weight of dextrin (Pinedex #1: manufactured by Matsuo Chemical Industries Co.) were heated to obtain uniform molten product. Then, the molten product was extruded to a filament shape into isopropyl alcohol cooled to −10° C. by using an extruder, rapidly quenched and then stirred and pulverized. Then, the pulverization product was removed with isopropyl alcohol by a centrifugal treatment, to obtain a granulated substance containing the polyphenol compound.

Example 20

Preparation of Deodorant Composition

The following polyphenol compound-containing granulated substance was prepared, the granulated substance was weighed by such an amount that the polyphenol compound content was 2 μmol, and then 100 μmol of sodium hydrogen carbonate and 0.5 μmol of magnesium chloride were added and mixed to obtain a deodorant composition.

Preparation of Polyphenol Compound-Containing Granulated Substance

A mixture of 10 kg of sorbitol and 0.2 kg of catechin (polyphenol powder GTP90: manufactured by Aiya Co.) was spontaneously dropped in a hopper, then moved horizontally by utilizing a horizontal screw at a number of rotation of the screw of 15 rpm and supplied between compression rollers. The catechin was compressed under the conditions at a roller compression pressure of 25 N/cm, with a roller distance of 0.5 mm, and at the number of rotation of roller of 15 rpm, to obtain a plate-like product. The plate-like product was cooled by a cold blow.

The cooling product was pulverized by a rotational pulverizer, and aligned for the size, to obtain a polyphenol compound-containing granulated substance.

Example 21

Preparation of Deodorant Composition

The following polyphenol compound-containing granulated substance was prepared, the granulated substance was weighed by such an amount that the polyphenol compound content was 2 μmol, and then 100 μmol of sodium hydrogen carbonate and 0.5 μmol of magnesium chloride were added and mixed, to obtain a deodorant composition.

Preparation of Polyphenol Compound-Containing Granulated Substance

After dissolving 15 kg of water, 8.9 kg of dextrin as an excipient (manufactured by Matsuya Chemical Industry Co., Ltd.), and 0.1 kg of an emulsifier (polyglycerin fatty acid ester), 1 kg of catechin (polyphenol powder GTP90: manufactured by Aiya Co.) were added and stirred and mixed by using a TK mixer, to obtain an emulsion. Then, the emulsion was spray-dried by a spray drier set to an inlet temperature of 180° C. and an exhaust temperature of 90° C., to obtain a polyphenol compound-containing granulated substance.

While the invention has been described in detail and with reference to specific embodiments thereof, it will be apparent to one skilled in the art that various changes and modifications can be made therein without departing from the scope thereof.

This application is based on Japanese patent application No. 2006-079559 filed Mar. 22, 2006, the entire contents thereof being hereby incorporated by reference.

Further, all references cited herein are incorporated in their entireties.

INDUSTRIAL APPLICABILITY

According to the invention, a deodorant composition capable of exhibiting a deodorizing effect in a short period of time when applied to a malodor component can be provided. In addition, a deodorant composition exhibiting an excellent deodorizing activity and excellent in the store stability can be provided. Further, since the deodorant composition of the invention is colorless or exhibits white or pale color, it scarcely undergoes restriction upon application as the deodorant. The invention can provide a novel deodorant composition used for elimination or reduction of malodors felt in daily life such as bad breath, odor in refrigerators, odor of raw garbage, odor in footwear cup board, body odor of human and animal, odor of feces and urine of human and animal, and malodor in factories or industrial liquid wastes.

The present invention provides a deodorant composition exhibiting an excellent deodorizing effect on various malodor components. The deodorant composition of the invention is excellent in the deodorizing effect on malodor components, for example, sulfur-containing compounds such as methyl mercaptan, hydrogen sulfide, and dimethyl sulfide and lower fatty acids such as butyric acid and isovaleric acid among malodor components, and is also excellent in the deodorizing effect on amine malodor components such as ammonia which are alkaline. Furthermore, since the method for preparing the deodorant composition is relatively simple and it has an advantage that the deodorant performance is maintained even after the deodorant composition is stored for a long time once the deodorant composition is prepared, the composition can be said to be a remarkably excellent deodorant composition.

The invention claimed is:

1. A deodorant composition consisting essentially of:
(a) a polyphenol compound,
(b) a basic substance, and
(c) a metal salt,
wherein the components (a), (b), and (c) are present as an admixture thereof;
wherein the polyphenol compound is at least one member selected from the group consisting of chlorogenic acid, gallic acid, catechin, rutin, and caffeic acid;
wherein the basic substance is at least one member selected from the group consisting of sodium carbonate, sodium hydroxide, sodium hydrogen carbonate, brine, lye, and a bleach;
wherein the metal salt is at least one member selected from the group consisting of magnesium chloride, calcium chloride, copper chloride, zinc chloride, and manganese sulfate,
wherein a polyphenol compound oxidase is not included in the deodorant composition,
wherein the amount of the polyphenol compound is from 1 to 50% by weight based on the deodorant composition, and
wherein the amount of the basic substance is such that, when the deodorant composition is dissolved in water to make an aqueous solution thereof, the aqueous solution has a pH of 7.0 or more.

2. A deodorant composition consisting essentially of:
(a) a granulated substance which contains a polyphenol compound,
(b) a basic substance, and
(c) a metal salt,
wherein the components (a), (b), and (c) are present as an admixture thereof;
wherein the polyphenol compound is at least one member selected from the group consisting of chlorogenic acid, gallic acid, catechin, rutin, and caffeic acid;

wherein the basic substance is at least one member selected from the group consisting of sodium carbonate, sodium hydroxide, sodium hydrogen carbonate, brine, lye, and a bleach;

wherein the metal salt is at least one member selected from the group consisting of magnesium chloride, calcium chloride, copper chloride, zinc chloride, and manganese sulfate, wherein a polyphenol compound oxidase is not included in the deodorant composition, wherein the amount of the polyphenol compound is from 1 to 50% by weight based on the deodorant composition, and wherein the amount of the basic substance is such that, when the deodorant composition is dissolved in water to make an aqueous solution thereof, the aqueous solution has a pH of 7.0 or more.

3. The deodorant composition according to claim 2, wherein the basic substance is at least one member selected from the group consisting of brine, lye, and a bleach.

4. A method for deodorizing a malodor, which comprises applying the deodorant composition according to claim 1 or 2 to a malodor component.

5. The method according to claim 4, wherein the malodor component comprises a sulfur-containing compound, a lower fatty acid, and/or an amine.

6. A deodorant composition consisting essentially of:
(a) a plant extract containing a polyphenol compound,
(b) a basic substance, and
(c) a metal salt, wherein the components (a), (b), and (c) are present as an admixture thereof;

wherein the plant extract containing a polyphenol compound is at least one member selected from the group consisting of green tea extract, coffee raw bean extract, apple extract, and grape pericarp extract;

wherein the basic substance is at least one member selected from the group consisting of sodium carbonate, sodium hydroxide, sodium hydrogen carbonate, brine, lye, and a bleach;

wherein the metal salt is at least one member selected from the group consisting of magnesium chloride, calcium chloride, copper chloride, zinc chloride, and manganese sulfate, wherein a polyphenol compound oxidase is not included in the deodorant composition, wherein the amount of the polyphenol compound is from 1 to 50% by weight based on the deodorant composition, and wherein the amount of the basic substance is such that, when the deodorant composition is dissolved in water to make an aqueous solution thereof, the aqueous solution has a pH of 7.0 or more.

7. A deodorant composition consisting essentially of:
(a) a granulated substance which contains a plant extract containing a polyphenol compound,
(b) a basic substance, and
(c) a metal salt, wherein the components (a), (b), and (c) are present as an admixture thereof;

wherein the plant extract containing a polyphenol compound is at least one member selected from the group consisting of green tea extract, coffee raw bean extract, apple extract, and grape pericarp extract;

wherein the basic substance is at least one member selected from the group consisting of sodium carbonate, sodium hydroxide, sodium hydrogen carbonate, brine, lye, and a bleach;

wherein the metal salt is at least one member selected from the group consisting of magnesium chloride, calcium chloride, copper chloride, zinc chloride, and manganese sulfate, wherein a polyphenol compound oxidase is not included in the deodorant composition, wherein the amount of the polyphenol compound is from 1 to 50% by weight based on the deodorant composition, and wherein the amount of the basic substance is such that, when the deodorant composition is dissolved in water to make an aqueous solution thereof, the aqueous solution has a pH of 7.0 or more.

8. A method for deodorizing a malodor, which comprises applying the deodorant composition according to claim 6 or 7 to a malodor component.

9. The method according to claim 8, wherein the malodor component comprises a sulfur-containing compound, a lower fatty acid, and/or an amine.

10. The deodorant composition according to claim 1, wherein each of the components (a), (b) and (c) is in a state of a solid product.

11. The deodorant composition according to claim 2, wherein each of the components (a), (b) and (c) is in a state of a solid product.

12. The deodorant composition according to claim 6, wherein each of the components (a), (b) and (c) is in a state of a solid product.

13. The deodorant composition according to claim 7, wherein each of the components (a), (b) and (c) is in a state of a solid product.

* * * * *